United States Patent [19]
Wiltshire et al.

[11] 3,955,136
[45] May 4, 1976

[54] MACHINE FOR DIELECTRICALLY DETECTING DEFECTS IN FLAT RUBBER STOCK

[75] Inventors: Arthur J. Wiltshire, Richmond Heights; Henry U. Ranallo, Euclid, both of Ohio

[73] Assignee: Structural Fibers, Inc., Chardon, Ohio

[22] Filed: Nov. 20, 1974

[21] Appl. No.: 525,486

[52] U.S. Cl. .................................. 324/54; 242/65; 340/259
[51] Int. Cl.² ................. G01R 31/12; B65H 17/08
[58] Field of Search ............... 324/54, 52; 340/259; 73/159; 242/65

[56] References Cited
UNITED STATES PATENTS

| | | | |
|---|---|---|---|
| 2,087,783 | 7/1937 | Savage | 324/54 |
| 2,194,078 | 3/1940 | Simonds | 242/65 |
| 2,890,409 | 6/1959 | Van Krevelen | 324/54 |
| 2,896,196 | 7/1959 | Hartford et al. | 73/159 X |
| 3,321,703 | 5/1967 | Tyszewicz | 324/54 |
| 3,695,540 | 10/1972 | Grantham | 242/65 |
| 3,792,458 | 2/1974 | Smith et al. | 324/54 X |

*Primary Examiner*—Gerard R. Strecker
*Attorney, Agent, or Firm*—McNenny, Farrington, Pearne & Gordon

[57] ABSTRACT

A machine and method for detecting and identifying the approximate location of air leak-causing defects in flat, thin rubber stock used to manufacture inflatable, expandable bags. The detection of air leak-causing defects is accomplished by continuously moving at a relatively constant rate the flat rubber stock to be tested between two cylindrical rollers. These two rollers are maintained at a voltage which will fluctuate in response to any air leak-causing defect passing between them. The machine disclosed is composed of a frame to which is mounted a feed spool and a take-up spool, numerous supports and guides, a set of two test rollers, a dielectric analyzer, and a marker which punches the edge of the rubber stock adjacent to the in-line location of a detected defect. The disclosed machine and method enable detection of small pin-hole sized defects often undetectable to the naked eye.

6 Claims, 5 Drawing Figures

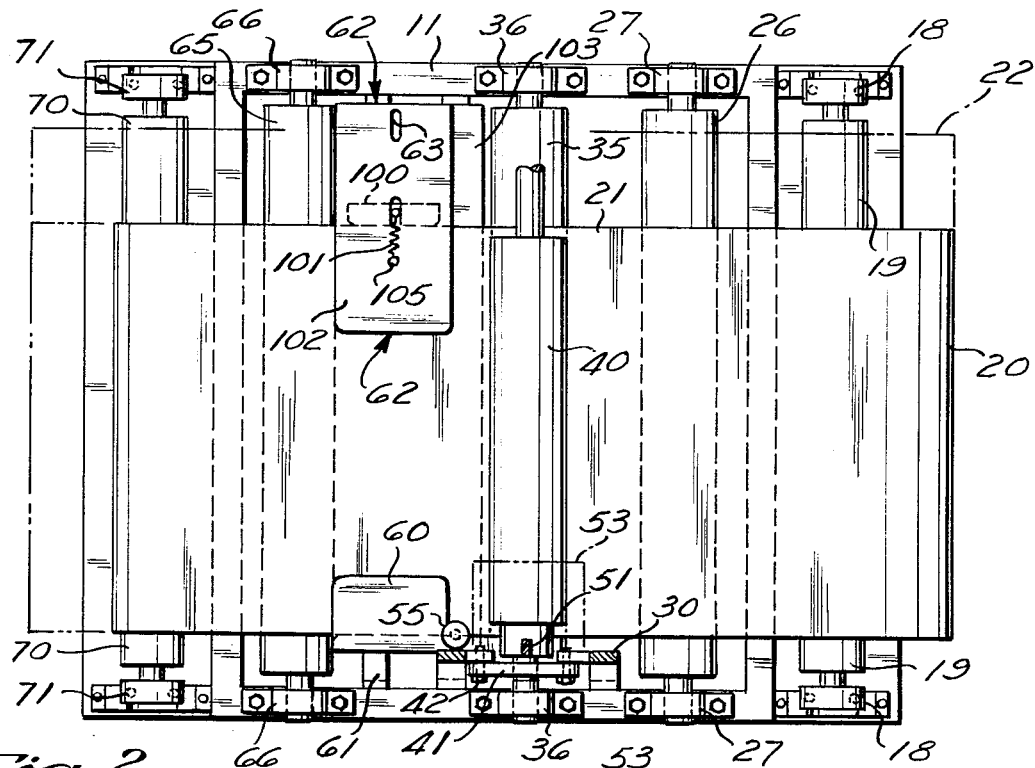
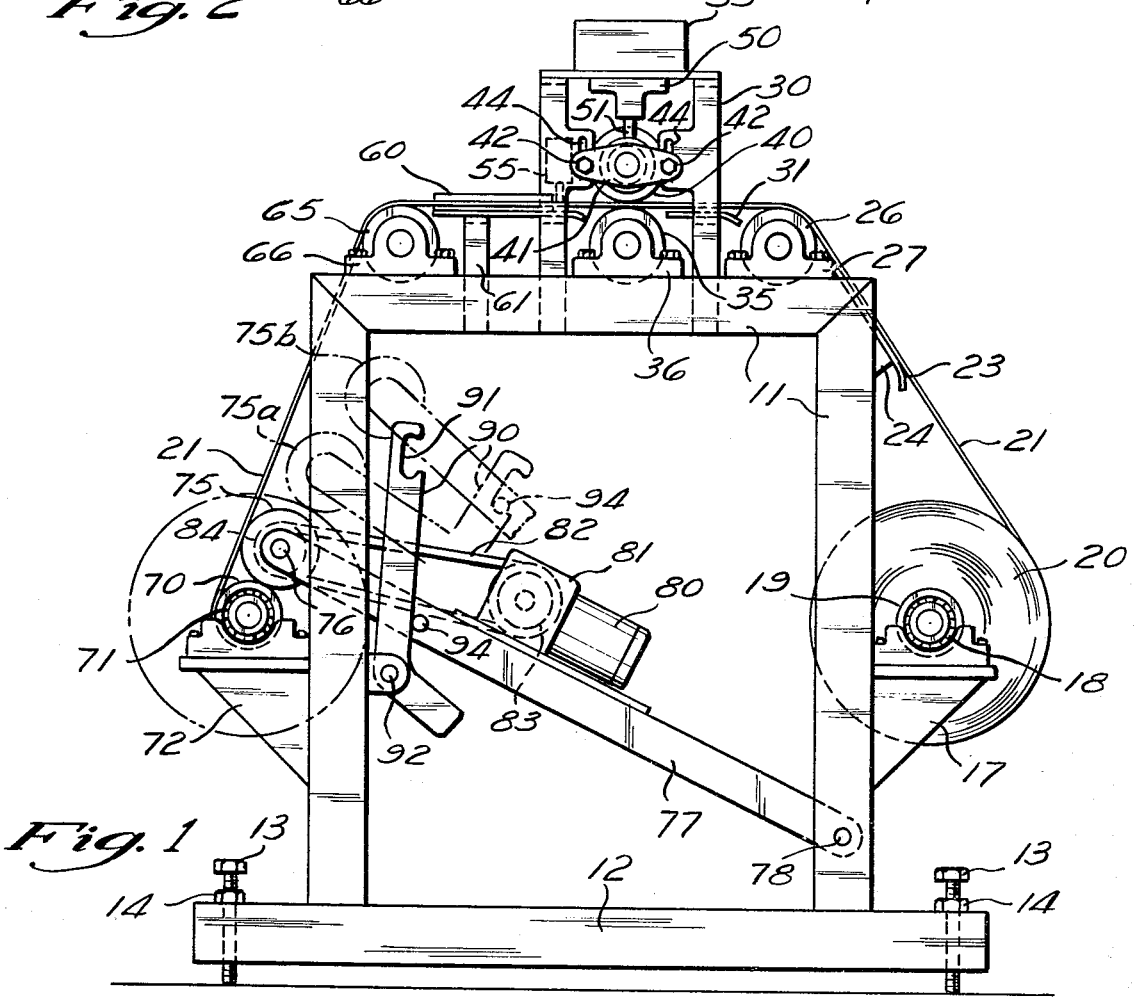

MACHINE FOR DIELECTRICALLY DETECTING DEFECTS IN FLAT RUBBER STOCK

BACKGROUND OF THE INVENTION

This invention relates generally to the testing of inflatable bags employed in the manufacture of fiber-reinforced plastic articles, such as tanks or the like, and more particularly to an apparatus and method for detecting and identifying the approximate location of defects in rubber stock which is to be formed into inflatable bags and used in the manufacture of such articles. In the manufacture of fiber-reinforced articles, randomly oriented fibers are formed in the approximate shape of the article to be molded and held in that shape by a resin binder. This preform, as it is called, is then encased within a rigid mold casing. An expandable bag, usually made from flat, thin rubber stock, which will define the interior shape of the finished article is placed within the laid up preform within the mold. The form is held in place in the mold by a suitably moderate pressure by inflating the bag with air to hold the fiber preform in place against the interior wall of the mold, and then the fiber preform is partially permeated with a thermosetting resin or the like. The bag is subsequently expanded by further inflation to compress the fiber form in such a manner as to distribute the resin throughout the fiber matting and achieve the results of pressure molding. The above-described process is set forth in U.S. Reissue Pat. No. 25,241 to Randolph.

It is essential that the expandable bag which is placed in the mold and inflated be absolutely airtight, since even a small pin hole-sized air leak will cause a structural defect in the wall of the finished fiber-reinforced article. Thus, it is desirable to detect and identify the location of air leak defects within the flat rubber stock used to manufacture the expandable bags. Once the defect is detected and located, that portion containing the defect can be cut from the rubber stock before it is used to manufacture the bags so that the resultant fiber-reinforced articles are free from structural defects caused by air leaks in the expandable bag.

In the past, detection of small air leak-causing defects in flat, thin rubber stock has been time-consuming and impractical. The disclosed invention solves these problems.

SUMMARY OF THE INVENTION

A method and a machine utilizing such method for detecting and identifying the location of air leak-causing defects in flat, thin rubber stock used in the manufacture of inflatable, expandable bags are disclosed.

Flat rubber stock can properly be termed a dielectric material, since it does not conduct current, but does permit the passage of the lines of force of an electrostatic field. Small cuts or punctures in the flat rubber stock will exhibit themselves as dielectric defects when the material is tested as to its dielectric qualities using the disclosed testing method. Thus, the detection of any dielectric defects and identification of their approximate locations will correspond to the detection and identification of actual or potential air leak-causing defects. Elimination of any dielectric defects will ensure an airtight bag manufactured from the tested rubber stock.

Detection of air leak-causing dielectric defects is accomplished by continuously moving at a relatively constant rate the flat rubber stock to be tested between two cylindrical rollers which are parallel and adjacent to each other, with their peripheries opposed, being movable relative to each other in a direction normal to their axes. The two rollers are each maintained at a separate, relatively stable voltage potential by a dielectric analyzer such that current will flow in the form of an electric arc between the roller surfaces but for the dielectric rubber stock's acting as an insulator between them. When a small cut or puncture extending through the rubber stock is present between the two rollers, an arc will jump from one roller to the other at the approximate location of the cut or puncture. Also, small surface defects, such as thin spots, which do not extend from one side to the other of the rubber stock may be exhibited as dielectric defects, depending on the test voltage used. This is desirable, since such a defect may develop into an air leak when the rubber stock is expanded by air pressure. When an arc indicative of an air leak-causing defect occurs, the voltage potential between the two rollers fluctuates instantaneously. This fluctuation is sensed by the analyzer, which triggers a device that marks the approximate location of the defect. The disclosed marking device is composed of a solenoid which punches the edge of the rubber stock adjacent to the in-line location of the defect. Thus, when an expandable bag is manufactured from the tested rubber stock, a punch mark calls attention to an air leak defect, often undetectable to the naked eye, which must be eliminated by cutting away and not using the area of rubber stock containing the defect.

The disclosed machine includes a feed spool which initially contains untested rubber stock and a take-up spool which is driven by a knurled cylinder mounted parallel and adjacent to the take-up spool, with the periphery of the cylinder opposed to the periphery of the spool. The cylinder and spool, which are gravity-biased, move relative to each other as a function of the amount of rubber stock wrapped on the take-up spool. While the rate of rotation differs between the take-up spool and the knurled cylinder as a function of the amount of rubber stock wrapped on the take-up spool, the rate at which the rubber stock is moved between the test rollers remains constant.

Attached to the frame of the machine are numerous rollers and guides which support and properly position the rubber stock between the two test rolls.

BRIEF DESCRIPTION OF THE DRAWINGS

FIG. 1 is a side view of a machine incorporating this invention;

FIG. 2 is a plan view of the machine illustrated in FIG. 1, with portions removed for clarity;

DETAILED DESCRIPTION OF THE DRAWINGS

Figure 3:
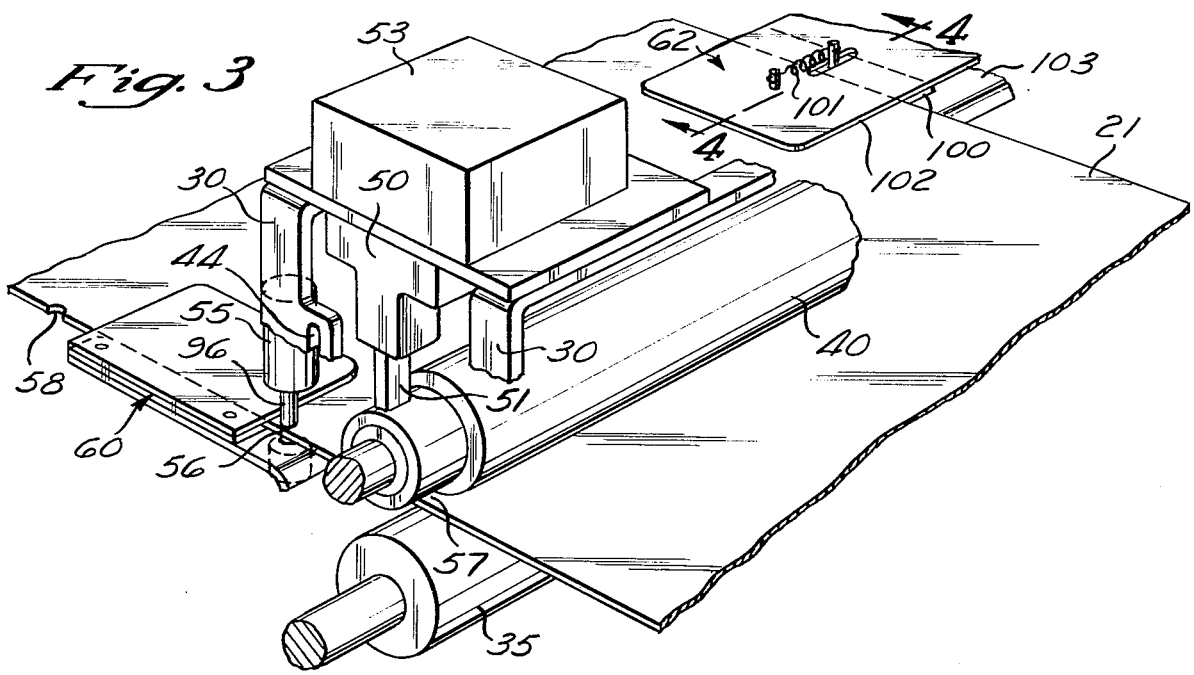
FIG. 3 is an enlarged, fragmentary, perspective view of a portion of the machine, illustrating a dielectric test means and an associated marker means.

Referring now to the drawings in greater detail, FIGS. 1 and 2 illustrate a base portion 12 of a frame 11 which can be leveled using leveling bolts 13 and securing the leveling bolts with lock nuts 14.

Mounted on one side of the frame is a removable feed spool 19 which is free to rotate while being held in position by ball bearing assemblies 18. The feed spool assembly 19 is also equipped with axial ball bushings so that the untested rubber on the feed spool 19 will float axially along its shaft to ensure a proper feed of the rubber stock, as will be described. The bearing assemblies 18 are secured to feed spool pedestals 17 which are fastened to the frame 11. Initially, a bulk amount of untested flat rubber stock 20 is wrapped around the feed spool 19. This bulk amount of rubber stock 20 is removed on a continuous basis as it feeds through the machine. As a single layer sheet of flat rubber stock 21 is pulled from the feed spool 19, it passes over a guide 23 attached to the frame 11 by a guide support 24. The rubber stock 21 then passes over a support roller 26 which is free to rotate about its longitudinal axis, being supported by bearing assemblies 27 which are fastened to the frame 11.

The rubber stock 21 then passes over a fixed support 31 which is attached to a superstructure 30, which in turn is mounted on a top portion of the frame 11. The rubber stock then passes between a ground test roller 35 and a hot test roller 40. The ground test roller 35 is free to rotate about its longitudinal exis, being supported by ground roller bearing assemblies 36 which are fastened to the frame 11. Preferably, the ground test roller 35 is electrically insulated from the frame 11, while being electrically connected to the negative or ground side of an electronic dielectric analyzer 50, which is protected by a cover 53. The analyzer 50 may be a commercially available unit, such as an analyzer available from the Slaughter Company of Ardmore, Ok.

The hot roller 40 is free to rotate about its longitudinal axis, being supported by hot roller bearing assemblies 41. The hot test roller 40 is electrically insulated from the superstructure 30 and the frame 11, while being electrically connected to the positive or hot side of the electronic dielectric analyzer 50. This electrical connection is accomplished through a spring-biased carbon brush 51 which extends from the dielectric analyzer 50 to a peripheral copper slip ring on a reduced peripheral section on one end of the hot roller 40. The hot roller 40 is free to float vertically by having its bearing assembly provided with pins 42 vertically slidable in slots 44. The floating action accommodates any variations in stock thickness.

A solenoid-driven punch and die 55 punches a notch in the edge of the rubber stock 21 in response to the detection of a defect between the hot test roll 40 and the ground test roll 35 by the electronic dielectric analyzer 50.

A fixed guide assembly 60 is attached to a guide assembly support 61 which is mounted on the frame 11. An adjustable guide assembly 62, being spring-biased, exerts a lateral force against the edge of the rubber stock 21, causing it to snug up against the fixed guide 60. These two guides maintain the rubber stock in the proper position as it moves between the ground test roller 35 and the hot test roller 40. An alternate guide slot 63 in the adjustable guide assembly 62 allows this assembly to be set up for a wider rubber stock 22, as schematically illustrated.

As earlier described, the feed spool 19, being provided with axial ball bearing assemblies within the spool, can shift axially in response to the lateral force exerted by the spring-biased guide assembly 62, such that the rubber stock 21 will be pulled from the feed spool in line with the test rollers. This ensures that the rubber stock will track properly through the hot roller and the ground roller. If the stock shifts from its illustrated position, arcing may obtain between those rollers.

Figure 4:
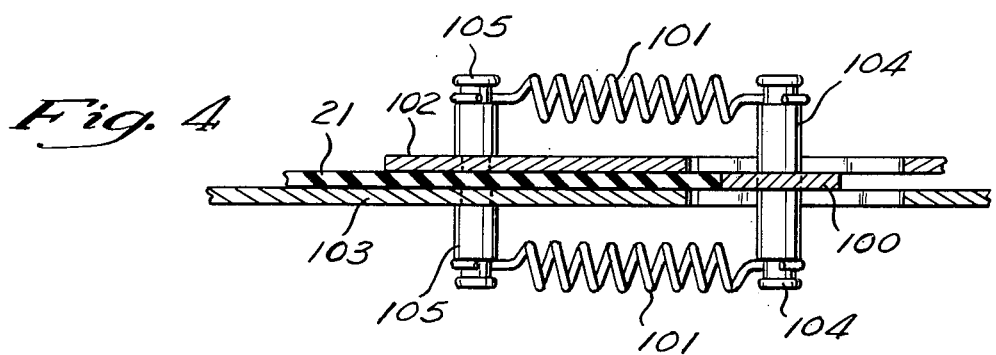
FIG. 4 is an enlarged, cross sectional view, the plane of the section being indicated by the line 4—4 in FIG. 3.

As is best illustrated in FIG. 4, the rubber stock 21 is sandwiched between a bottom guide plate 103 and a top guide plate 102. A sliding bias plate 100 is pulled against the edge of the rubber stock 21 as it is moving through the machine. A constant force is applied to the edge of the rubber by bias springs 101. One end of the bias springs is attached to fixed guide plate studs 105, while the other end of the springs is attached to the movable bias plate studs 104.

This adjustable guide assembly continuously causes the rubber to snug up against the fixed guide assembly 60, and therefore the rubber stock 21 is always in a proper position between the ground test roller 35 and the hot test roller 40.

After passing between the guide assembly, the rubber then passes over another support roller 65 which rotates about its longitudinal axis, being held in position by bearing assemblies 66 which are secured to the frame 11. The rubber stock 21 is then wrapped around a driven take-up spool 70 which rotates about its axis, being held in position by take-up spool bearing assemblies 71, which in turn are mounted to pedestal supports 72 attached to the frame 11.

Figure 5:
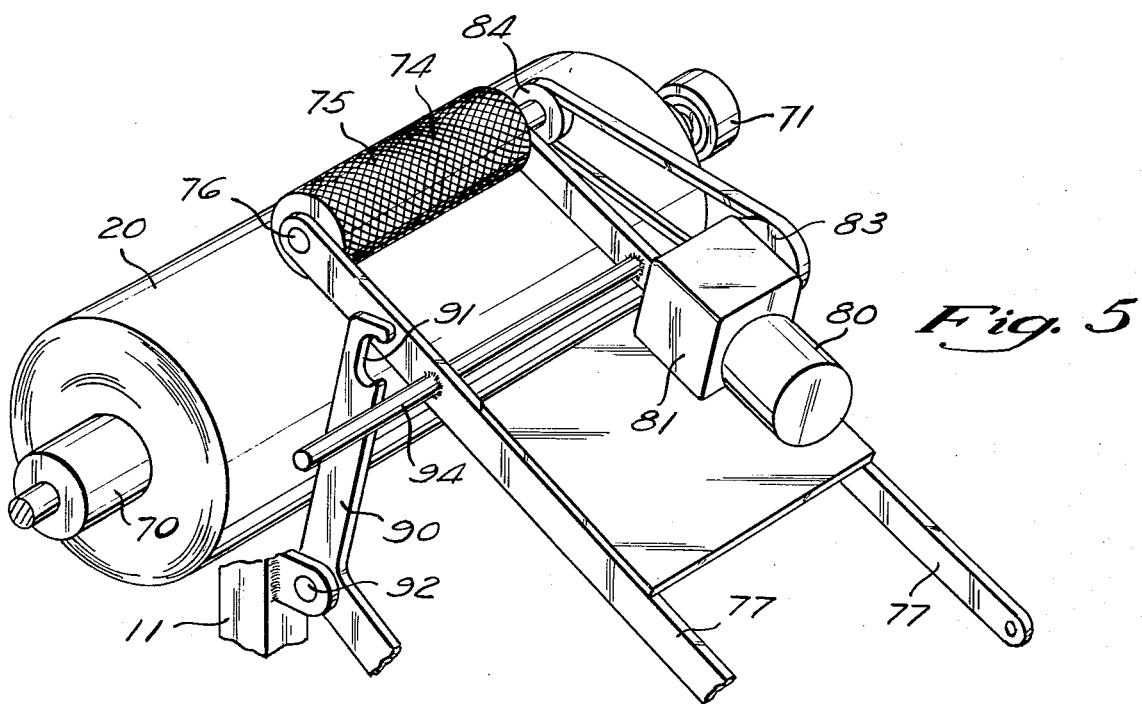
FIG. 5 is an enlarged, perspective view of a take-up spool and drive means according to this invention.

Referring now to FIG. 5, a knurled cylinder 75 rotates the take-up spool 70. This knurled cylinder 75 is held against the take-up spool 70 by gravity. The knurled cylinder 75 is free to rotate and is held in position by bearing assemblies 76, which in turn are mounted to an elongated member 77 which is pivotally fastened to the frame by pivot bolts 78. The knurled cylinder 75 is rotated by an electric motor 80 in combination with a transmission 81. The transmission driving pulley 83 is connected to a driven pulley 84 mounted on one end of the knurled cyiinder 75 by a drive belt 82.

It can be seen how the knurled peripheral surface 74 of the cylinder 75 is held by gravity against the take-up spool 70. While the rate of rotation of the knurled cylinder remains constant, the rate of rotation of the take-up spool will vary as a function of the amount of bulk rubber stock 20 wrapped around the take-up spool 70. However, the rate at which the rubber stock moves between the hot test roller 40 and the ground test roller 35 will always remain the same for a given constant speed of the knurled cylinder 75.

A retaining arm 90 is pivotally mounted to the frame 11 by a bushing assembly 92. After all of the stock is on the takeup spool and the cylinder 75 is in the phantom position designated by the reference numeral 75a, the cylinder is raised by hand to the phantom position designated by the reference numeral 75b. A retaining notch 91 in the arm 90 may then be brought into engagement with the retaining arm 94. Once the retaining rod 94 is engaged in the retaining notch 91, the drive assembly is held in position while the take-up spool is removed.

Referring now to FIG. 3, a more detailed view of the ground roller 35 and the hot roller 40 and their associated detecting and identifying assemblies can be seen. The punch mark 58 is indicative of the detection of the dielectric defect within the rubber stock. If a dielectric defect is detected within the area 57 between the rollers, the solenoid 55 actuates the punch 96 which punches the edge of the rubber stock at the location 56. This results in a punch notch 58. The punch notch will be offset a distance equal to the distance between the centerline of the roller 40 and the centerline of the punch 96. The operator will later cut the rubber at the line of defect, taking into consideration the amount of offset.

Although a preferred embodiment of this invention is illustrated, it is to be understood that various modifications and rearrangements of parts may be resorted to without departing from the scope of the invention claimed herein.

What is claimed is:

1. A machine for continuously detecting and identifying the approximate location of dielectric defects in a specified amount of planar nonconductive material comprising a frame, a plurality of supports fastened to said frame so as to maintain said nonconductive material in position, guides attached to said frame so as to properly position said nonconductive material, means mounted on said frame for continuously moving said nonconductive material, said means including a gravity biased drive cylinder adapted to contact said nonconductive material, a dielectric analyzer mounted on said frame for detecting said dielectric defects, said analyzer designed to establish an area of relatively stable voltage potential between opposite sides of said planar nonconductive material, said voltage potential fluctuating in response to a dielectric defect within said area of voltage potential, said dielectric analyzer including a first metal cylindrical roller, said first roller being fixed on a lateral axis, and a second metal cylindrical roller, said second roller being movable along said lateral axis, each roller being maintained at a separate electric potential and mounted substantially parallel and adjacent to each other with the peripheries of said rollers opposed, said second roller being gravitybiased toward said first roller wherein the distance between said rollers is a function of the thickness of said planar nonconductive material which passes in a linear direction between said rollers, said lateral axis being perpendicular to said linear direction, and means to mark said material in response to fluctuations in said voltage potential for identifying the approximate location of said dielectric defects in said nonconductive material.

2. A machine as set forth in claim 1, wherein said supports include at least two idler rollers, an idler feed spool and a driven take-up spool.

3. A machine as set forth in claim 2, wherein said idler feed spool is supported by axial ball bearing assemblies such that said spool is free to move laterally along its longitudinal axis as it rotates.

4. A machine for continuously detecting and identifying the approximate location of dielectric defects in a specified amount of planar nonconductive material comprising a frame, a plurality of supports fastened to said frame so as to maintain said nonconductive material in position, guides attached to said frame so as to properly position said nonconductive material, a take-up spool attached to said frame driven in response to a drive cylinder mounted parallel and adjacent to said take-up spool with the periphery of said cylinder opposed to the periphery of said spool, said cylinder being gravitybiased toward said spool, said cylinder and spool being movable relative to each other in a direction normal to their axes and as a function of the amount of material wrapped on said spool, a dielectric analyzer mounted on said frame for detecting said dielectric defects, said analyzer including two adjacent metal rollers, one being gravity biased toward the other, designed to establish an area of relatively stable voltage potential between opposite sides of said nonconductive material, said voltage potential fluctuating in response to a dielectric defect within said area of voltage potential, and means to mark said material in response to fluctuations in said voltage potential for identifying the approximate location of said dielectric defects in said nonconductive material.

5. A machine as set forth in claim 4, wherein the outside peripheral surface of said cylinder is knurled.

6. A machine as set forth in claim 5, wherein said spool and cylinder are gravity-biased to maintain relative motion between said spool and said cylinder.

* * * * *